United States Patent [19]

Nique et al.

[11] Patent Number: 4,874,754
[45] Date of Patent: Oct. 17, 1989

[54] NOVEL 19-NOR-STEROIDS

[75] Inventors: Francois Nique, Pavillons sous Bois; Lucien Nedelec, Le Raincy; Marie-Madeleine Bouton, Paris; Daniel Philibert, La Varenne Saint-Hilaire, all of France

[73] Assignee: Roussel Uclaf, Paris, France

[21] Appl. No.: 157,417

[22] Filed: Feb. 17, 1988

[30] Foreign Application Priority Data

Feb. 18, 1987 [FR] France ............... 87 02072

[51] Int. Cl.⁴ .................. A61K 31/58; A61K 31/56; C07J 1/00
[52] U.S. Cl. .................. 514/178; 260/397.3; 260/397.4; 260/397.5; 514/177; 514/173; 514/182; 540/23
[58] Field of Search ............... 260/397.3, 397.4, 397.5; 540/23; 514/172, 173, 177, 178, 182

[56] References Cited

U.S. PATENT DOCUMENTS 3,673,225 6/1972 De Jongh .................. 260/397.3

Primary Examiner—Douglas W. Robinson
Assistant Examiner—Joseph A. Lipovsky
Attorney, Agent, or Firm—Bierman & Muserlian

[57] ABSTRACT

Novel 19-nor-steroids of the formula

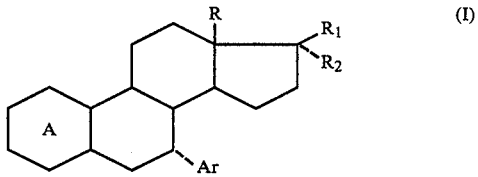

wherein the A ring is either

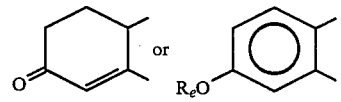

Re is selected from the group consisting of hydrogen, acyl and optionally substituted alkyl of 1 to 6 carbon atoms, R is methyl or ethyl, $R_1$ is selected from the group consisting of hydroxyl, protected hydroxyl, acyloxy and alkoxy, $R_2$ is selected from the group consisting of hydrogen, alkyl of 1 to 8 carbon atoms, alkenyl and alkynyl of 2 to 8 carbon atoms, acyl, aralkyl of 7 to 15 carbon atoms, the substituents other than hydrogen being optionally substituted or $R_1$ and $R_2$ together form a group selected from the group consisting of

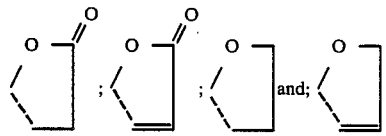

$A_r$ is an optionally substituted 5- or 6-membered aryl and their salts with non-toxic, pharmaceutically acceptable bases and acids having antiproliferative, anti-estrogenic and/or estrogenic properties.

12 Claims, No Drawings

NOVEL 19-NOR-STEROIDS

STATE OF THE ART

Related applications are commonly assigned U.S. patent applications Ser. No. 743,792 filed June 12, 1985 and Ser. No. 746,176 filed June 18, 1985.

OBJECTS OF THE INVENTION

It is an object of the invention to provide the novel compounds of formula I and their non-toxic, pharmaceutically acceptable salts and a process for their preparation.

It is another object of the invention to provide novel antiproliferatve compositions and to provide a method of inducing antiproliferative cell activity in warm-blooded animals.

These and other objects and advantages of the invention will become obvious from the following detailed description.

THE INVENTION

The novel compounds of the invention are selected from the group consisting of 19-nor-steroids of the formula

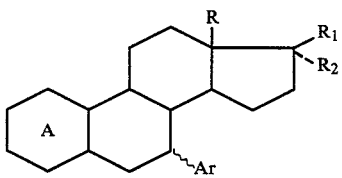

wherein the A ring is either

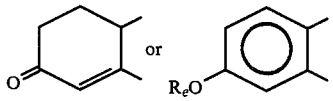

Re is selected from the group consisting of hydrogen, acyl and optionally substituted alkyl of 1 to 6 carbon atoms, R is methyl or ethyl, $R_1$ is selected from the group consisting of hydroxyl, protected hydroxyl, acyloxy and alkoxy, $R_2$ is selected from the group consisting of hydrogen, alkyl of 1 to 8 carbon atoms, alkenyl and alkynyl of 2 to 8 carbon atoms, aryl, aralkyl of 7 to 15 carbon atoms, the substituents other than hydrogen being optionally substituted or $R_1$ and $R_2$ together form a group selected from the group consisting of

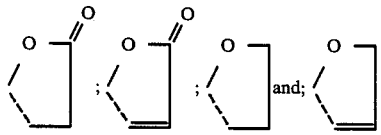

$A_r$ is an optionally substituted 5- or 6-membered aryl and their salts with non-toxic, pharmaceutically acceptable bases and acids.

Examples of alkyl are methyl, ethyl, propyl, isopropyl, butyl, sec-butyl, tert-butyl, pentyl, hexyl, 2-methylpentyl and 2,2-dimethylpentyl. Examples of alkenyl are vinyl, propenyl, allyl, isopropenyl, 2-methylallyl, isobutenyl and butenyl. Examples of alkynyl are ethynyl, propynyl, propargyl, isobutynyl and butynyl.

Examples of acyl are acetyl, propionyl, butyryl and benzoyl. Examples of alkoxy include the alkyls mentioned above, and especially methoxy, ethoxy, propyloxy, isopropyloxy and butyloxy.

In formula I the term aryl includes carbocyclic and heterocyclic groups. Among 5-membered groups are thienyl, furyl, thiazolyl, pyrrolyl, oxazolyl, imidazolyl, pyrazolyl, (1,2,3- or 1,2,4-)triazolyl, tetrazolyl, isothiazolyl and isoxazolyl. Among 6-membered groups are phenyl, pyridinyl pyridazinyl, pyrimidinyl and pyrazinyl.

Among preferred aryls are phenyl, furyl and thienyl and aralkyl is preferably benzyl, these groups optionally being substituted with alkyl, alkoxy, alkylthio, aminoalkyl or dialkylamino radicals mentioned above.

The term "optionally substituted" as applied to the alkyl, alkenyl, alkynyl, aryl or aralkyl preferably comprises at least one of the following: halogen such as fluorine, chlorine, bromine and iodine, alkyl such as methyl, ethyl, propyl, isopropyl, butyl, isobutyl, tert-butyl for the aryl and aralkyl, alkoxy such as methoxy, ethoxy, propyloxy, isopropyloxy and butyloxy, alkylthio such as methylthio, ethylthio, propylthio, isopropylthio and butylthio, amino, alkylamino such as methylamino or ethylamino, dialkylamino such as dimethyl-amino, diethylamino, methyl-ethylamino, each of the dialkyl-amino optionally being in oxidized form, aminoalkyl such as aminomethyl or aminoethyl, dialkylaminoalkyl such as dimethyl-aminomethyl or dimethylamino-ethyl, dialkylaminoalkyloxy such as dimethylaminoethyloxy, optionally acylated hydroxyl, for example acetoxy, or a group of the formula

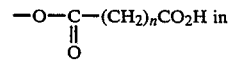

in which n=2 to 5, acyl such as acetyl, propionyl, butyryl, benzoyl, free or esterified carboxy, such as alkoxycarbonyl, for example methoxycarbonyl or ethoxycarbonyl, cyano, trifluoromethyl and aryl or aralkyl, optionally substituted.

When $R_e$ contains a substituent, it is preferably amino or a dialkylamino such as dimethylamino. The term "optionally protected hydroxyl" denotes the traditional protective groups such as acyl, for example acetyl, chloroacetyl and trifluoroacetyl, tetrahydropyranyl and silyls such as trimethylsilyl and tert-butyldimethylsilyl.

Depending on the nature of the substituents borne by $R_2$ and Ar, the products of formula I may form salts with acids or bases. Thus, if at least one of $R_2$ and Ar contains a salifiable amino, the products of formula I can form salts with acids. Examples of suitable acids are hydrochloric acid, hydrobromic acid, nitric acid, sulfuric acid, phosphoric acid, acetic acid, formic acid, propionic acid, maleic acid, fumaric acid, succinic acid, tartaric acid, citric acid, oxalic acid, glyoxylic acid and aspartic acid, alkenesulfonic acids such as methane- and ethanesulfonic acids, arylsulfonic acids such as benzene- and p-toluenesulfonic acids and arylcarboxylic acids such as benzoic acid.

If at least one of $R_2$ or A contains a carboxyl, it can be salified with a residue of a base. Examples of suitable salts are sodium, potassium, lithium, calcium, magnesium or ammonium salt. Among organic bases, methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine and N-methylglucamine may be mentioned.

Among the preferred compounds of the invention are those of formula I wherein A is

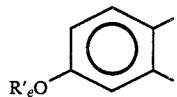

and Re is hydrogen or alkyl of 1 to 4 carbon atoms, those wherein Ar is (a) either phenyl optionally substituted with at least one member of the group consisting of halogen, alkyl, alkoxy and alkylthio of 1 to 4 carbon atoms, amino, alkylamino, dialkylamino, dialkylaminoalkoxyl, hydroxyl, acyl, free, esterified or salified carboxyl, cyano, trifluoromethyl, phenyl and benzyl optionally substituted with at least one alkyl of 1 to 4 carbon atoms, (b) or a heterocyclic selected from the group consisting of thienyl, furyl, thiazolyl, isothiazolyl, oxaxolyl, isoxazolyl, thiadiazolyl, pyridyl and piperidinyl and those wherein $R_1$ is hydroxyl optionally protected or acylated, and $R_2$ is alkyl, alkenyl or alkynyl, each optionally substituted with a member selected from the group consisting of halogens, hydroxyl, carboxyl optionally esterified or salified and cyano.

Specific preferred compounds are: 7α-{4-[2-(dimethylamino)-ethoxy]-phenyl}-Δ$^{1,3,5(10)}$-estratriene-3,17β-diol, 7α-{4-[2-(dimethylamino)-ethoxy]-phenyl}-17β-hydroxy-Δ$^4$-estren-3-one; 7β-{4-[2-(dimethylamino)-ethoxy]-phenyl}-Δ$^{1,3,5(10)}$-estratriene-3,17β-diol; 7β-{4-[2-(dimethylamino)-ethoxy]-phenyl}-17β-hydroxy-Δ$^4$-estren-3-one; 7α-[4-(dimethylamino)-phenyl]-Δ$^{1,3,5(10)}$-estratriene-3,17β-diol; 7α-(4-methoxyphenyl)-Δ$^{1,3,5(10)}$-estratriene-3,17β-diol; 7α-[4-(methylthio)-phenyl]-Δ$^4$-estren-17β-ol-3-one and 7α-[4-methylthio)-phenyl]-Δ$^{1,3,5(10)}$-estratriene-3,17β-diol.

The novel process of the invention for the preparation of the compounds of formula I comprises reacting a compound of the formula

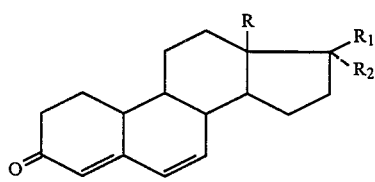

wherein R, $R_1$ and $R_2$ have the above definitions with a member of the group consisting of (a) a compound of the formula Ar-Mg-Hal in the presence of a cuprous salt, (b) a compound of the formula Ar$_2$CuLi and (c) a compound of the formula Ar$_2$CuCNLi$_2$ wherein Ar has the above definition and Hal is halogen to obtain a compound of the formula

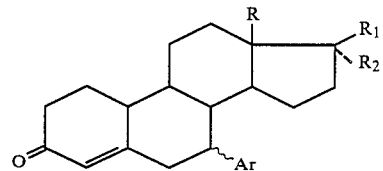

where appropriate in the form of a mixture of 7α- and 7β-isomers and optionally separating the same, optionally treating the latter with an aromatizing agent to obtain a compound of the formula

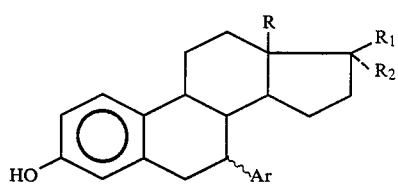

optionally reacting the latter with an alkylating agent to obtain a compound of the formula

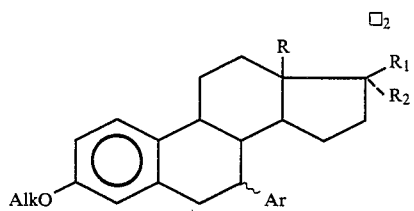

wherein Alk is alkyl of 1 to 6 carbon atoms and optionally subjecting the compounds of formulae $I_A$, $I_B$, and $I_{B2}$, depending on the nature of Ar and $R_2$, to the action of a or base acid to form the corresponding salts.

In a preferred embodiment of the process of the invention, Hal is chlorine, bromine or iodine, preferably bromine. The cuprous salt used is the chloride, bromide, iodide or cyanide, or the cuprous bromide/cuprous dimethyl sulfide complex. The reaction medium can then be subjected to a strong acid such as hydrochloric acid, nitric acid or sulfuric acid. The cuprous salt is preferably prepared in situ by reacting cupric chloride with lithium bromide but a Lewis acid optionally used can be boron trifluoride.

When a cupro-lithium compound of the formula Ar$_2$CuLi is used, the latter is also preferably prepared in situ by the action of cuprous iodide on Ar-Li, which is prepared from the halide Ar-Hal. The product of the formula Ar$_2$CuCNLi may be prepared by the action of cuprous cyanide on Ar-Li.

The aromatizing agent which is preferably used for converting the products of formula $I_A$ to the product of formula $I_{B1}$ may be chosen from the following reagents:

(a) The product of formula $I_A$ is first treated with a halogenating agent and then with a dehydrohalogenating agent such as cuprous bromide/lithium bromide in a solvent such as acetonitrile. (b) The product of formula $I_A$ is treated with a strong base such as butyllithium, the lithium enolate formed is blocked with a reagent such as tert-butyldimethylsilyl chloride, and the product thereby obtained is then dehydrogenated with a reagent such as 2,3-dichloro-5,6-dicyanobenzoquinone.

The alkylation of the products of formula $I_{B1}$ to obtain the products of formula $I_{B2}$ is carried out in the usual way such as using an alkyl halide or sulfate but the alkyl iodide is preferably used. When it is desired to separate the two isomers of formula $I_4$, the separation is performed under the usual conditions using techniques of crystallization or chromatography. The formation, where appropriate, of salts with acid or bases is also performed under the usual conditions.

Another process for preparing the products of formula I comprises reacting a compound of the formula

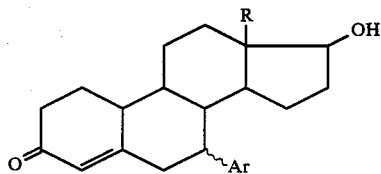

wherein R and Ar have the above definition, corresponding to a product of formula $I_4$ in which $R_1$ is hydroxyl and $R_2$ is hydrogen, with a reagent for blocking the 3-keto group—for example an enol ether or an acetal—to obtain a compound of the formula

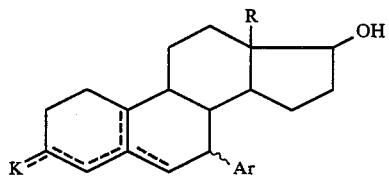

wherein K and the broken lines denote a protected keto group, preferably a product of the formulae

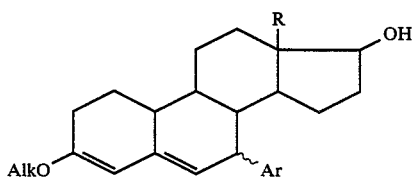

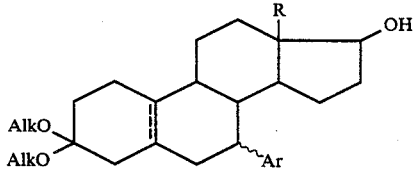

wherein Alk is alkyl and the broken lines denote a double bond at 5(6) or 5(10), reacting the compound of formula IV with an oxidizing agent to obtain a product of the formula

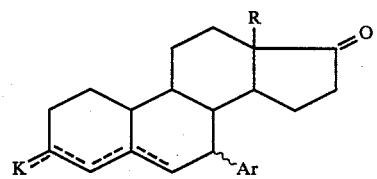

which product is reacted either with an organometallic derivative derived from $R_2$ which is alkyl, alkenyl or alkynyl of up to 8 carbon atoms or an aryl or aralkyl of up to 15 carbon atoms, each of alkyl, alkenyl, alkynyl, aryl or aralkyl optionally substituted, or first with an organometallic derivative of the formula —C≡C—CH$_2$OH in which the hydroxyl group is optionally protected, and then, in any order, optionally with a deprotecting reagent and a reagent for total or partial reduction, and then with a cyclizing or oxidizing reagent, or first with a reagent of the formula

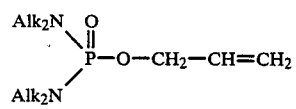

in the presence of a strong base to obtain, respectively, the products of the formula

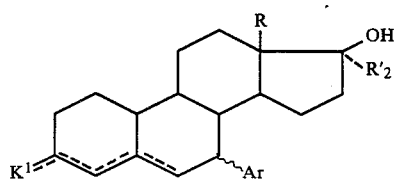

wherein $R'_2$ has the meanings of $R_2$ other than hydrogen and K' and the broken lines denote an optionally protected 3-keto-$\Delta^4$, and the products of the formula

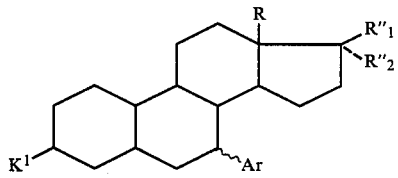

wherein $R_1''$ and $R_2''$ together form

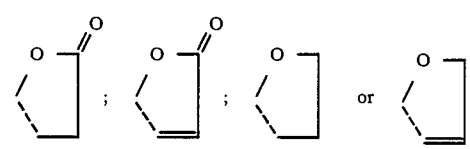

which products of formulae VI$_A$ and VI$_B$ are reacted, where appropriate, with a deprotecting reagent when K' is a group that protects the 3-keto-$\Delta^4$ to obtain a product of the formula

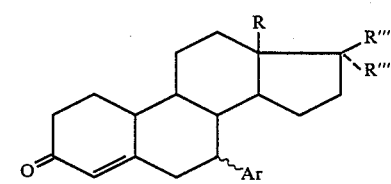

wherein $R_1'''$ and $R_2'''$ have the above definitions for $R_1$ and $R_2$ other than $R_2$ being hydrogen The products of formulae $I_D$ wherein $R_1'''$ is OH may be optionally subjected to a reagent for protection, acylation or alkylation of the 17β-OH. The products of the formula $I_D$. as well as the corresponding products $I_D$ in which the 17β-OH has been protected, acylated or alkylated, constitute the products of formula $I_A$. which can then be treated as described above.

The protection of the 3-keto-$\Delta^4$ group of the product of formula $I_C$ is preferably accomplished in the form of an enol ether by the action of an alkyl orthoformate such as ethyl orthoformate in the presence of p-toluenesulfonic acid. The oxidizing agent which is reacted with the product of formula IV to obtain a product of formula V may be chosen from Jones' reagent, pyridinium dichromate and pyridinium chlorochromate. It is also possible to use the Oppenauer oxidation reaction in the presence of cyclohexanone and aluminium isopropylate in toluene under reflux.

The organometallic compound whch is reacted with the product of formula V is preferably a magnesium compound. When the alkyl, alkenyl, alkynyl, aryl or aralkyl to be introduced contains a reactive group, this group may be protected by the usual methods. The reaction is performed according to the usual methods. It is preferably performed in the presence of a cerium halide such as $CeCl_3$ when $R_2$ is aryl. The same applies to the addition of a reagent of formula —CH=CH—CH$_2$OH, in which hydroxyl is preferably protected by a reagent such as tetrahydropyranyl or tert-butyl.

The reagent for total reduction which leads to the substituent —(CH$_2$)$_3$—OH is hydrogen in the presence of a catalyst such as palladium on charcoal or a rhodium-based catalyst such as Wilkinson's reagent. To obtain a partial reduction leading to the substituent —CH=CH—CH$_2$OH, hydrogen is used with a poisoned catalyst such as palladium on barium sulfate poisoned with pyridine or triethylamine.

The cyclization reaction which leads to the products containing

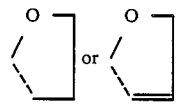

at the 17-position is carried out in the presence of p-toluenesulfonyl chloride and pyridine. The oxidation reaction which leads in situ to the cyclization and to the production of the products containing

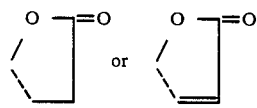

at the 17-position is carried out using the oxidizing agents mentioned above.

The action of the allyl tetraalkylphosphorodiamidate, preferably the tetramethyl, is performed according to the method described by STURTZ et al in Synthesis, 1980, p. 289. The strong base present during the reaction is preferably butyllithium but it is also possible to work in the presence of diazabicyclooctane (DABCO) or a crown ether.

The products of formulae $VI_A$ and $VI_B$ can, depending upon of K', be products of formula I. When K' is K, that is to say a protected 3-keto-$\Delta^4$, the deprotection can be carried out by the usual methods, particularly in acid medium such as aqueous hydrochloric acid.

The reactions for protection, acylation or alkylation of the 17$\beta$-OH group are carried out by the usual methods. The reaction is performed, for example, using an acyl halide such as acetyl chloride or a mixed or symmetrical anhydride such as acetic anhydride.

The pharmacological compositions of the invention are comprised of a pharmacologically effective amount of at least one compound of formula I and its salts with non-toxic, pharmaceutically acceptable acids and bases and an inert pharmaceutical carrier or excipient. The compositions may be in the form of tablets, dragees, gelatin capsules, granules, suppositories injectable solutions or suspensions, ointments, creams and gels.

Examples of suitable excipients are talc, gum arabic, lactose, starch, magnesium stearate, cocoa butter, aqueous or non-aqueous vehicles, fats of animal or vegetable origin, paraffinic derivatives, glycols, various wetting, dispersant or emulsifying agents and preservatives.

The compositions possess antiproliferative, antiestrogenic and estrogenic activity and are useful in the treatment of hormone-dependent carcinomas such as, for example, mammary carcinoma and its metastases as well as for use in the treatment of benign breast tumors. The estrogenic properties which may also be possessed by the compositions make them suitable for use also in the treatment of disorders linked to folliculin deficiency, for example amenorrhoea, dysmenorrhoea, repeated abortion and premenstrual disorders, as well as the treatment of menopause.

The novel method of the invention for inducing antiproliferative activity in warm-blooded animals, including humans, comprises administering to warm-blooded animals an amount of at least one compound of formula I and its salts with non-toxic, pharmaceutically acceptable acids and bases sufficient to induce antiproliferative activity. The compounds may be administered orally, rectally, parenterally or topically. The usual daily dose is 0.015 to 1.35 mg/kg depending on the conditions treated, the method of administration and the specific compound.

The starting compounds of formula II are known or can be prepared by known methods such as the above procedure of converting the compounds of formula $I_C$ to compounds of formula $I_D$ starting from the compound of the formula

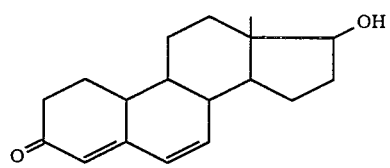

described in U.S. Pat. Nos. 2,739,974 and 3,099,664.

In the following examples there are described several preferred embodiments to illustrate the invention. However, it is to be understood that the invention is not intended to be limited to the specific embodiments.

EXAMPLE 1

17$\beta$-acetoxy-7$\beta$-{4-[2-dimethylamino)-ethoxy]-phenyl}-$\Delta^4$-estren-3-one and
17$\beta$-acetoxy-7$\alpha$-{4-[2-(dimethylamino)-ethoxy]-phenyl}-$\Delta^4$-estren-3-one (1) Preparation of the organomagnesium compound 1.32 g of magnesium turnings and 6 ml of anhydrous tetrahydrofuran were mixed under an inert atmosphere and 11 g of 4-[2-(dimethylamino)-ethyl]-bromobenzene dissolved in 30 ml of anhydrous tetrahydrofuran were introduced at 40° C. over the course of approximately 50 minutes after priming with 2 drops of dibromoethane. The mixture was stirred for 2 hours at 40° C. and a crystallization was noted.

(2) 1,6 addition 1.5 g of anhydrous cuprous chloride were added to the suspension of organomagnesium compound obtained and the mixture was stirred at 20° C. for 30 minutes. 6.6 g of 17β-acetoxy-Δ$^{4,6}$estradien-3-one dissolved in 30 ml of anhydrous tetrahydrofuran were introduced at −35° C. over the course of approximately 45 minutes and the reaction suspension was acidified after one hour with 20 ml of 5N aqueous hydrochloric acid solution. The mixture was poured into a saturated aqueous sodium bicarbonate solution and the mixture was extracted with ethyl acetate. The extract was washed with aqueous ammonium chloride solution and with saline solution, dried and concentrated to dryness by distillation under reduced pressure. The 12.6 g of residue were chromatographed on silica and eluted under nitrogen pressure with a mixture of methylene chloride, isopropanol and ammonia solution (95:5:0.5) and then with a mixture of methylene chloride, isopropanol and ammonia solution (90:10:1) to obtain 5.62 g of 17β-acetoxy-7β-{4-[2-dimethylamino)-ethoxy]pheny}-Δ$^4$-estren-3-one (product I) and 2.53 g of 17β-acetoxy-7α-{4-[2-(dimethylamino)-ethoxy]-phenyl}-Δ$^4$-estren-3-one (product II).

NMR Spectrum (CDCl$_3$) in ppm:

| | |
|---|---|
| H of 18-Me | 0.82 (s) |
| H of O Ac | 2.02 (s) |
| H of N | 2.33 (s) |
| H of O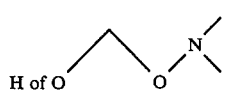 | 2.73 (t) |
| H of O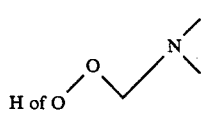 | 4.06 (t) |
| 17α″H | 4.49 (t) |
| H4 | 5.81 |
| H of 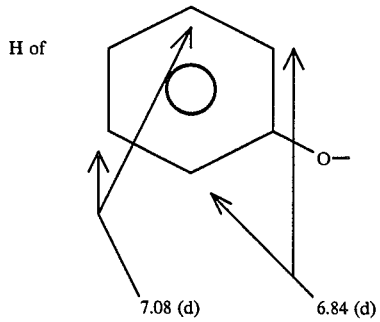 | |

NMR Spectrum (CDCl$_3$) in ppm:

H of 18-Me     0.88 (s)

H of OAc

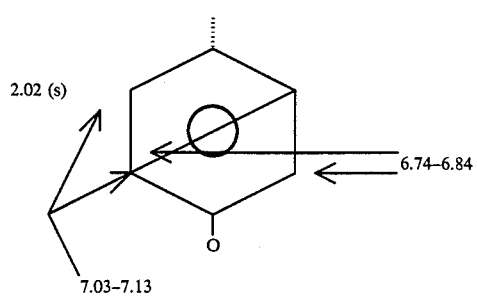

| | |
|---|---|
| H of —N(/\) | 2.35 (s) |
| H of O—\/—O—N(/\) | 2.73 (t) |
| 7βH | 3.06 |
| H of O—\/—N(/\) | 4.07 (t) |
| 17αH | 4.43 (t) |
| H4 | 5.88 |

EXAMPLE 2

17β-acetoxy-7α-{4-[2-(dimethylamino)-ethoxy]-phenyl}-Δ$^{1,3,5(10)}$estratrien-3-ol 2.33 g of product II (7α) obtained in Example 1, 100 ml of acetonitrile, 3.44 g of cupric bromide and 470 mg of lithium bromide were mixed under an inert atmosphere and the mixture was stirred at 75° C. for 105 minutes and was cooled to 20° C. The mixture was alkalinized with sodium bicarbonate and extracted with chloroform. The extract was washed with aqueous ammonium chloride solution, dried and concentrated to dryness by distillation under reduced pressure. The 2.4 g of residue were chromatographed on silica and eluted with a mixture of ethyl acetate and triethylamine (8:2) to obtain 1.18 g of expected product.

| NMR spectrum (CDCl$_3$) in ppm: | |
|---|---|
| 20 H of 18 Me | 0.84 (s) |
| H of OAc | 2.03 (s) |
| H of —N(/\) | 2.35 (s) |
| H of O—\/—O—N (↑ on O) | 2.75 |
| 7beta H | 3.07 JH7 H8~3 Hz |
| H of H de O (↑) —\/—N | 4.04 |
| Aromatic H atoms | 6.63 to 7.20 |

EXAMPLE 3

7α-{4-[2-(dimethylamino)-ethoxy]-phenyl}-Δ$^{1,3,5(10)}$estratriene-3,17β-diol 1.18 g of product of Example 2, 12 ml of methanol and 3.7 ml of 2M methanolic potassium hydroxide solution were mixed under an inert atmosphere and the solution obtained was stirred at 20° C. for 1 hour and concentrated to dryness by distillation under reduced pressure. The residue was acidified with 4 ml of 2N aqueous hydrochloric acid solution and alkalinized with sodium bicarbonate and extracted with ethyl acetate. The extract was washed with saline solution, dried and concentrated to dryness by distillation under reduced pressure. The 1.08 g of residue were chromatographed on silica and eluted with a mixture of ethyl acetate and triethylamine (8:2) to obtain 1.02 g of expected product with a specific rotation of [α]$_D$= +1.5° (1% in chloroform)

| NMR spectrum (CDCl$_3$) in ppm: | |
|---|---|
| H of 18-Me | 0.78 (s) |
| H of N(/\) | 2.35 (s) |
| H of O—\/—N | 2.75 (t) |
| 17alpha H | 3.60 |
| H of O—\/—N | 4.02 (t) |
| Aromatic H atoms from | 6.61 to 7.23 |

EXAMPLE 4

7α-{4-[2-(dimethylamino)-ethoxy]-phenyl}-Δ$^4$-estren-17β-ol-3-one 480 mg of product II (7α) obtained in Example 1, 5 ml of methanol and 1 ml of 2M methanolic potassium hydroxide solution were mixed under an inert atmosphere and the solution was stirred at 20° C. for 3 hours 30 minutes. The methanol was removed by distillation under reduced pressure and water was added to the residue. The mixture was extracted with ethyl acetate and with methylene chloride and the organic phases were washed with saline solution, dried and concentrated to dryness by distillation under reduced pressure. The 340 mg of residue were chromatographed on silica and eluted with a mixture of ethyl acetate and triethylamine (9:1) to obtain 160 mg of expected product.

320 mg (originating from one operation) of product thereby obtained were chromatographed on 90 g of Lichroprep Si 60(5–20 um) and eluted with a mixture of ethyl acetate and triethylamine (9:1) to obtain 180 mg of pure expected product.

| NMR spectrum (CDCl₃) in ppm: | |
|---|---|
| H of 18-Me | 0.83 (s) |
| H of —N< | 2.32 (s) |
| H of O-CH₂-CH₂-N | 2.71 (t) |
| H of O-CH₂-CH₂-N, H4 | 4.04 (t) 5.88 |
| | 7.06 (d) |
| | 6.82 (d) |

EXAMPLE 5

17β-acetoxy-7β-{4-[2-(dimethylamino)-ethoxy]-phenyl}-Δ¹,³,⁵⁽¹⁰⁾-estratrien-3-ol 2.4 g of product I (7β) of Example 1, 100 ml of acetonitrile, 3.7 g of cupric bromide and 500 mg of lithium bromide were mixed under an inert atmosphere and the mixture was stirred at 75° C. for 90 minutes. The temperature was brought back to 20° C. and the mixture was alkalinized with sodium bicarbonate and extracted with chloroform. The extract was washed with aqueous ammonium chloride solution, dried and concentrated to dryness by distillation under reduced pressure. The 2.55 g of residue were chromatographed on silica and eluted with a mixture of ethyl acetate and triethylamine (8:2) to obtain 800 mg of expected product.

| NMR spectrum (CDCL₃) in ppm: | |
|---|---|
| H of 18-Me | 0.76 (s) |
| H of OAc | 2.02 (s) |
| H of N< | 2.32 (s) |
| H of O-CH₂-CH₂-N | 2.71 (t) |
| H of O-CH₂-CH₂-N | 4.03 (t) |
| Aromatic H atoms | from 6.58 to 7.21 |

EXAMPLE 6

7β-{4-[2-(dimethylamino)-ethoxy]-phenyl}-Δ¹,³,⁴⁽¹⁰⁾-estratriene-3,17β-diol 800 mg of the product of Example 5, 8 ml of methanol and 2.5 ml of 2M methanolic potassium hydroxide solution were mixed under an inert atmosphere and the solution obtained was stirred at 20° C. for 3 hours 30 minutes. The methanol was removed by distillation under reduced pressure and the mixture was acidified with 2N aqueous hydrochloric acid solution then alkalinized with sodium bicarbonate and extracted with ethyl acetate. The extract was washed with saline solution, dried and concentrated to dryness by distillation under reduced pressure. The 720 mg of residue were chromatographed on silica and eluted with a mixture of ethyl acetate and triethylamine (8:2) to obtain 660 mg of expected product with a specific rotation of $[\alpha]_D = +25°$ (c=1% in chloroform).

| NMR spectrum (CDCL₃) in ppm: | |
|---|---|
| H of 18-Me | 0.70 (s) |
| H of N< | 2.33 (s) |
| H of O-CH₂-CH₂-N | 2.77 (t) |
| 17 alpha H | 3.62 (t) |
| H of O-CH₂-CH₂-N | 4.04 (t) |
| Aromatic H atoms | from 6.50 to 7.22 |

EXAMPLE 7

7β-{4-[2-(dimethylamino)-ethoxy]-phenyl}-Δ⁴-estren-17β-ol-3-one 480 mg of product I of Example 1, 5 ml of ethanol and 1 ml of 2M methanolic potassium hydroxide solution were mixed under an inert atmosphere and the mixture was stirred at 20° C. for 90 minutes and concentrated to dryness by distillation under reduced pressure. Water was added to the residue and the mixture was extracted with ethyl acetate. The extract was washed with saline solution, dried and concentrated to dryness by distillation under reduced pressure. The 410 mg of residue were chromatographed on silica and eluted with a mixture of ethyl acetate and triethylamine (9:1) to obtain 215 mg of crude product. 215 mg were dissolved in 1 ml of boiling ethyl acetate and the solution was seeded and cooled to 0° C. The precipitate formed was isolated by suction filtration washed and dried to obtain 160 mg of expected product melting at 149° C.

Crystallization for analysis: 265 mg (two batches) were dissolved in 4 ml of ethyl acetate at reflux and the mixture was filtered, concentrated until crystallization began and cooled to 0° C. The precipitate formed was isolated by suction filtration washed with ice-cold ethyl acetate and dried to obtain 215 mg of expected product melting at 149° C.

| NMR spectrum (CDCl$_3$) in ppm: | |
|---|---|
| H of 18-Me | 0.77 (s) |
| H of N$<$ | 2.36 (s) |
| H of O~~~N | 2.74 (t) |
| H of H de O~~~N | 4.07 (t) |
| 4H | 5.81 |
| 7.07(d) [structure] 6.84(d) | |

EXAMPLE 8

7α-[4-(dimethylamino)-phenyl]-Δ$^4$-estren-17β-ol-3-one
and
7β-[4-(dimethylamino)-phenyl]-Δ$^4$-estren-17β-ol-3-one (1) Preparation of organomagnesium compound 2.1 g of magnesium turnings and 5 ml of anhydrous tetrahydrofuran were mixed under an inert atmosphere, followed, after priming, at 35° C., by the introduction over approximately 45 minutes of 18 g of 4-bromo-dimethylaniline dissolved in 90 ml of tetrahydrofuran and the mixture was stirred for a further hour at 20° C. The titre by iodometry was 0.65N.

(2) 1,6 addition

The solution of organomagnesium compound was cooled to 40° C. and a solution of 25 g of cuprous iodide and 11.7 g of lithium bromide in 100 ml of tetrahydrofuran was added over approximately 20 minutes. The mixture was stirred for 15 minutes and 17 ml of boron trifluoride etherate were added at −50° C. over approximately 15 minutes to the thick suspension obtained. The mixture was stirred for 15 minutes and 8 g of Δ$^{4,6}$-estradien-17β-ol-3-one melting at 187 C. dissolved in 80 ml of tetrahydrofuran were introduced over approximately 5 minutes. The suspension was stirred at −50 C. for 3 hours and then left to stand for 16 hours. The reaction mixture was then poured into twofold-diluted standard strength hydrochloric acid and the mixture was stirred for 20 minutes at 20° C., alkalinized with 80 ml of twofold-diluted standard strength ammonia solution and stirred. Settling was allowed to occur and the product was extracted with ethyl acetate. The extract was washed with aqueous sodium chloride solution, dried and concentrated to dryness by distillation under reduced pressure. The 13 g of residue were chromatographed on silica and eluted with a mixture of cyclohexane and ethyl acetate (1:1) to obtain 7.85 g of crude product which was chromatographed on silica. Elution with a mixture of acetonitrile and water (6:4) yielded 3.38 g of 7α-[4-(dimethylamino)-phenyl]-Δ$^4$-estren-17β-ol-3-one (I) melting at 190° C. and 1.9 g of 7β-[4-(dimethylamino)-phenyl]-Δ$^4$-estren-17β-ol-3-one (II).

830 mg of (I) were dissolved in 4 ml of methylene chloride and 8 ml of isopropyl ether were added. The mixture was concentrated until crystallization began and brought to 0° C. The precipitate formed was isolated by suction filtration, washed with isopropyl ether and dried to obtain 715 mg of purified expected product I melting at 202° C.

| NMR spectrum (CDCl$_3$) in ppm: | |
|---|---|
| H of the 18-Me | 0.83 (s) |
| H of N$<$CH$_3$/CH$_3$ | 2.92 (S) |
| 4H | 2.92 |
| Aromatic H atoms | 6.66 (d) |
|  | 7.06 (d) |
| Constants for the product II (7beta) | |
| NMR spectrum (CDCl$_3$) in ppm: | |
| H of the 18-methyl | 0.77 (s) |
| H N$<$CH$_3$/CH$_3$ | 2.93 (s) |
| 17 alpha H | 3.53 |
| 4H | 5.82 |
| Aromatic H atoms | 6.72 (d) |
|  | 7.15 (d) |

EXAMPLE 9

7α-[4-(dimethylamino)-phenyl]-17β-[dimethyl-1,1-dimethylethyl)-silyloxy]-Δ$^4$-estren-3-one 1.36 g of 7α-[4-(dimethylamino)-phenyl]-Δ$^4$-estren-17β-ol-3-one of Example 8 were dissolved at 20° C. under an inert atmosphere in 6 ml of dimethylformamide and 630 mg of dimethyl-(1,1-dimethylethyl)-chlorosilane and 593 mg of imidazole were added. The reaction mixture was stirred at 45° C. for 50 minutes, cooled and poured into water. The product was extracted with ethyl acetate and the extract was washed with saline solution, dried and concentrated to dryness by distillation under reduced pressure. The 2.15 g of residue were chromatographed on silica and eluted with a mixture of cyclohexane and ethyl acetate (7:3) to obtain 1.54 g of expected product.

| NMR spectrum (CDCl$_3$) in ppm: | |
|---|---|
| H of SiMe$_2$ | 0.055 (s) |
| H of 18-methyl | 0.89 (s) |
| H of tBu | 0.96 (s) |

-continued

| NMR spectrum (CDCl₃) in ppm: | |
|---|---|
| H of N(Me)(Me) | 3.03 (s) |
| 17 alpha H | 3.5 |
| 4H | 5.97 |
| Aromatic H atoms | 6.72 (d) |
| | 7.12 (d) |

EXAMPLE 10

7α-[4-(dimethylamino)-phenyl]-17β-[dimethyl-(1,1-dimethylethyl)-silyloxy]-Δ$^{1,3,5(10)}$-estratrien-3-ol (1) Preparation of the silyl enol ether 0.42 ml of diisopropylamine and 8 ml of tetrahydrofuran were mixed under an inert atmosphere and 1.85 ml of a 1.65N solution of n-butyllithium in hexane were added at 0° C. over approximately 10 minutes. The mixture was stirred for 30 minutes and 394 mg of 7α-[4-(dimethylamino)-phenyl]-17β-[dimethyl-(1,1-dimethylethyl)-silyloxy]-Δ⁴-estren-3-one dissolved in 4 ml of tetrahydrofuran were added at −60° C. over approximately 5 minutes. The mixture was stirred for 1 hour and 0.63 ml of trimethylsilyl chloride were added. The temperature was allowed to return to 20° C. and a solution was obtained.

(2) Aromatization 340 mg of 2,3-dichloro-5,6-dicyanobenzoquinone and 0.5 ml of water were added to the solution of silyl enol ether of Example 9 and the mixture was stirred for 20 hour at 20° C. and filtered. The filtrate was poured into caustic soda and the product was extracted with ethyl acetate. The extract was washed with saline solution, dried and concentrated to dryness by distillation under reduced pressure. The 840 mg of residue were chromatographed on silica and eluted with a mixture of toluene and ethyl acetate (9:1) to obtain 116 mg of expected product melting at 214° C.

| IR spectrum (chloroform) in cm-1: | |
|---|---|
| Phenol type OH | 3,599 cm¹ |
| Aromatic | 1,613, 1,582, 1,556, 1,521, 1,501 |
| NMR spectrum (CDCl₃) in ppm: | |
| H of Si Me₂ | 0.017 (s) |
| H of 18-Me | 0.77 (s) |
| H of tBu | 0.88 (s) |
| H of NMe₂ | 2.9 (s) |
| Aromatic H atoms | 6.56 to 7.28 |

EXAMPLE 11

7α-[4-(dimethylamino)-phenyl]-Δ$^{1,3,5(10)}$-estratriene-3,17β-diol 420 mg of 7α-[4-(dimethylamino)-phenyl]-17β-[dimethyl-(1,1-dimethylethyl)-silyloxy]-Δ$^{1,3,5(10)}$-estratrien-3-ol of Example 10 were dissolved at 20° C. under an inert atmosphere in 8 ml of ethanol and 2 ml of 40% strength aqueous hydrofluoric acid solution were added. The mixture was stirred at 20° C. for 4 hours 30 minutes, alkalinized with sodium bicarbonate and extracted with ethyl acetate. The extract was washed with aqueous sodium chloride solution, dried and concentrated to dryness by distillation under reduced pressure. The 340 mg of residue melting at 262° C. were dissolved in 20 ml of ethyl acetate under reflux and the mixture was filtered. The filtrate was concentrated until crystallization began, brought to 0° C. and stirred. The precipitate formed was isolated by vacuum filtration, washed with ethyl acetate and dried to obtain 280 mg of expected product melting at 262° C.

| NMR spectrum (CDCl₃ + DMSO) in ppm: | |
|---|---|
| H of the 18-Me | 0.78 (s) |
| H of NMe₂ | 2.87 (s) |
| H of 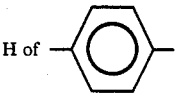 | 6.53 (d) |
| | 6.91 (d) |
| H1 | 7.13 (d) |
| H2 and H4 | 6.58 to 6.73 |
| 1H, mobile | 8.11 |

EXAMPLE 12

7α-(4-methoxyphenyl)-Δ4-estren-17β-ol-3-one and 7β-(4-methoxyphenyl)-Δ⁴-estrene-17β-ol-3-one 12.5 g of cuprous iodide and 5.5 g of anhydrous lithium bromide dissolved in 50 ml of tetrahydrofuran were introduced at −40° C. into 50 ml of a 0.8M solution of the magnesium derivative of 4-bromoanisole in tetrahydrofuran and the mixture was stirred for 15 minutes at −40° C. 8.5 ml of boron trifluoride etherate were added at −50 C. over approximately 10 minutes, and the mixture was stirred at −50° C. for 15 minutes. 4 g of Δ$^{4,6}$-estradiene-17β-ol-3-one melting at 187° C. dissolved in 50 ml of tetrahydrofuran were introduced and the suspension obtained was stirred at −50° C. for 3 hours. 25 ml of twofold-diluted standard strength hydrochloric acid were added and the temperature was allowed to rise to room temperature. Ethyl acetate was added and the mixture was stirred. Settling was allowed to occur and the organic phase was washed with ammonia solution and with saline solution, dried and concentrated to dryness by distillation under reduced pressure. The 6.7 g of residue were chromatographed on silica and eluted with a mixture of cyclohexane and ethyl acetate (1:1) to obtain 4.8 g of crude product. The 4.8 g were made into a paste with 10 ml of ethyl acetate and the precipitate was isolated by vacuum filtration, washed with ethyl acetate and dried to obtain 2.43 g of 7α-(4-methoxyphenyl)-Δ⁴-estren-17β-ol-3-one (product I) melting at 260° C.

The mother liquors from the paste preparation were taken to dryness by distillation under reduced pressure to obtain 2.29 g of 7β-(4-methoxyphenyl)-Δ⁴-estren-17β-ol-3-one (product II).

Constants for the product I (7α)

| NMR Spectrum (CDCl₃) in ppm: | |
|---|---|
| H of 18-Me | 0.83 (s) |
| 17 H | 3.48 (t) |
| H of OMe | 3.78 (s) |
| 4 H | 5.86 |
| Aromatic H atoms | 6.76 (d) |
| | 7.06 (d) |

Constants for the product II (7β)

| NMR Spectrum (CDCl$_3$) in ppm: | |
| --- | --- |
| H of 18-Me | 0.77 (s) |
| 17 H | 3.50 (t) |
| H of OMe | 3.78 (s) |
| 4H | 5.79 |
| Aromatic H atoms | 6.79 (d) |
| | 7.06 (d) |

EXAMPLE 13

17β-[dimethyl-(1,1-dimethylethyl)-silyloxy]-7α-(4-methoxyphenyl)-Δ$^4$-estren-3-one 2.3 g of 7α-(4-methoxyphenyl)-Δ$^4$-estrene-17β-ol-3-one (product I) of Example 12, 12 ml of dimethylformamide, 1.09 g of dimethyl-(1,1-dimethylethyl)-chlorosilane and 1.03 g of imidazole were mixed under an inert atmosphere and the reaction mixture was stirred at 40° C. for 3 hours 15 minutes (dissolution) brought to 20° C. and poured into water. The product was extracted with ethyl acetate and the extract was washed with aqueous sodium chloride solution, dried and concentrated to dryness by distillation under reduced pressure. The 3.84 g of residue were chromatographed on silica and eluted with a mixture of cyclohexane and ethyl acetate (1:1) to obtain 2.72 g of expected product.

| NMR Spectrum (CDCl$_3$) in ppm: | |
| --- | --- |
| H of SiMe$_2$ | 0.05 (s) |
| H of 18-Me | 0.78 (s) |
| H of tBu | 0.85 (s) |
| 17α H | 3.39 |
| H of OMe | 3.77 (s) |
| 4H | 5.84 |
| Aromatic H atoms | 6.76 (d) |
| | 7.06 (d) |

EXAMPLE 14

17β-[dimethyl-(1,1-dimethylethyl)-silyloxy]-7α-(4-methoxyphenyl)-Δ$^{1,3,5(10)}$-estratrien-3-ol (1) Preparation of the silyl enol ether 0.35 ml of diisopropylamine and 7 ml of tetrahydrofuran were mixed under an inert atmosphere and 1.7 ml of 1.65N solution of n-butyllithium in hexane were added at −5° C. over approximately 5 minutes. The mixture was stirred for 30 minutes at −5° C. and 530 mg of 17β-[dimethyl-(1,1-dimethylethyl)-silyloxy]-7α-(4-methoxyphenyl)-Δ$^4$-estren-3-one of Example 13 dissolved in 4 ml of tetrahydrofuran were added at −60° C. over approximately 10 minutes. The mixture was stirred at −65° C. for 90 minutes and 0.7 ml of trimethylsilyl chloride were added. The temperature was allowed to return to 20° C. and the mixture was stirred for 1 hour at 20° C.

(2) Dehydrogenation 366 mg of 2,3-dichloro-5,6-dicyanobenzoquinone and 0.7 ml of water were added to the reaction mixture and the mixture was stirred for 16 hours at 20° C. and poured into 2N aqueous sodium hydroxide solution. The product was extracted with ethyl acetate and the extract was washed with aqueous sodium chloride solution, dried and concentrated to dryness by distillation under reduced pressure. The 880 mg of residue were chromatographed on silica and eluted with a mixture of toluene and ethyl acetate (9:1) to obtain 295 mg of expected product.

| NMR Spectrum (CDCl$_3$) in ppm: | |
| --- | --- |
| H of Si Me$_2$ | 0.017 (s) |
| H of 18-Me | 0.79 (s) |
| H of tBu | 0.91 (s) |
| 17α H | 3.50 |
| H of OMe | 3.78 (s) |
| Aromatic H atoms | 6.7 to 7.27 |

EXAMPLE 15

7α-(4-methoxyphenyl)-Δ$^{1,3,5(10)}$-estratriene-3,17β-diol 646 mg of 17β-[dimethyl-(1,1-dimethylethyl)-silyloxy]-7α-(4-methoxyphenyl)-Δ$^{1,3,5(10)}$-estratrien-3-ol of Example 14 were dissolved at 20° C. under an inert atmosphere in 50 ml of acetonitrile and 5 ml of 40% strength aqueous hydrofluoric acid solution were added. A gum formed which was dissolved by adding 40 ml of acetonitrile and the mixture was left at 20° C. for 16 hours, concentrated to distillation under reduced pressure, neutralized with sodium bicarbonate and extracted with ethyl acetate. The extract was washed with aqueous sodium chloride solution, dried and concentrated to dryness by distillation under reduced pressure. The 1.02 g of residue were chromato-graphed on silica and eluted with a mixture of cyclohexane and ethyl acetate (1:1) to obtin 370 mg of expected product melting at 190° C. and then 227° C.

Crystallization for analysis

The 370 mg were dissolved in 12 ml of ethyl acetate at reflux and the mixture was filtered. The filtrate was concentrated until crystallization began, brought to 0° C. and stirred. The precipitate formed for isolated by vacuum filtration, washed with ethyl acetate and dried to obtain 300 mg of purified expected product melting at 190° C. and the 228° C.

| NMR Spectrum (CDCl$_3$) in ppm | |
| --- | --- |
| H of 18-Me | 0.8 (s) |
| H of OMe | 3.74 (s) |
| H, mobile | 4.71 |
| Aromatic H atoms from | 6.61 to 7.22 |

EXAMPLE 16

7α-[4-(methylthio)-phenyl]-Δ$^4$-estren-17β-ol-3-one and 7β-[4-methylthio)-phenyl]-Δ$^4$-estren-17β-ol-3-one (1). Preparation of the organomagnesium compound 2 g of magnesium turnings and 2 ml of tetrahydrofuran were mixed under an inert atmosphere at 20° C. and 15 g of 4-bromothioanisole dissolved in 45 ml of tetrahydrofuran were introduced, after priming with dibromomethane, over approximately 1 hour. During the introduction, the temperature was held at 50° C. and the mixture was stirred for a further hour at 50° C. and then titrated by iodometry. The titer of the organomagnesium compound was 1.1M.

(2). 1,6 Addition 50 ml of 1.1M organomagnesium compound obtained above, 15 g of cuprous iodide and 7 g of lithium bromide dissolved in 40 ml of tetrahydrofuran were mixed under an inert atmosphere and the mixture was stirred for 15 minutes. 10 ml of boron trifluoride etherate were introduced at −50° C. over approximately 5 minutes and the mixture was stirred for 15 minutes at −50° C. 4.9 g of $\Delta^{4,6}$-estradien-17$\beta$-ol-3-one melting at 187° C. dissolved in 50 ml of tetrahydrofuran were introduced over approximately 15 minutes and the suspension obtained was stirred for 1 hour. The reaction mixture was poured into a mixture of aqueous ammonium chloride solution and ice and the mixture was stirred. 5M aqueous ammonia solution was added and settling was allowed to occur. The product was extracted with ethyl acetate and the extract was washed with saturated aqueous sodium chloride solution, dried and concentrated to dryness by distillation under reduced pressure. The 14.5 g of residue were chromatographed on silica under nitrogen pressure and eluted with a mixture of cyclohexane and ethyl acetate (1:1) to obtain 2.89 g of a mixture of epimers melting at 220° C.

Crystallization

The 2.89 g were dissolved in 35 ml of boiling methylene chloride and 35 ml of isopropyl ether were added. The mixture was concentrated until crystallization began, cooled to 0° C. and stirred. The precipitate formed was isolated by vacuum filtration, washed with isopropanol ether and dried to obtain 1.65 g of 7$\alpha$-[4-(methylthio)-phenyl]$\Delta^4$estren-17$\beta$-ol-3-one (product I).

400 mg of product I were dissolved in 20 ml of boiling methanol and the mixture was filtered. The filtrate was concentrated until crystallization began and chilled. The precipitate formed was isolated by vacuum filtration, washed and dried to obtain 330 mg melting at 244° C.

Constants for product I

| NMR Spectrum (CDCl$_3$) in ppm: | |
|---|---|
| H of the 18-methyl | 0.82 (s) |
| H of SCH$_3$ | 2.45 (s) |
| 17$\alpha$ H | 3.49 (t) |
| H4 | 5.87 |
| Aromatic H atoms | 7.0 to 7.2 |

The mother liquors of crystallization of product I were taken to dryness to obtain 1.24 g of product II containing ¾ of 7$\beta$-isomers, namely 7$\beta$-[4-methylthio)-phenyl-$\Delta^4$-estren-17$\beta$-ol-3-one.

Constants for product II

| NMR Spectrum (CDCl$_3$) in ppm: | |
|---|---|
| H of the 18-methyl | 0.77 (s) |
| H of SCH$_3$ | 2.47 (s) |
| 17$\alpha$ H | 3.51 (s) |
| H4 | 5.80 |
| Aromatic H atoms | 7.0 to 7.2 |

EXAMPLE 17

17$\beta$-[dimethyl-(1,1-dimethylethyl)-silyloxy]-7$\alpha$-[4-(methylthio)-phenyl]-$\Delta^4$-estren-3-one 0.9 g of 7$\beta$-[4-(methylthio)-phenyl]-$\Delta^4$-estrene-17$\beta$-ol-3-one of Example 16, 500 mg of dimethyl-(1,1-dimethylethyl)-chlorosilane and 476 mg of imidazole were suspended under an inert atmosphere in 5 ml of dimethylformamide and the mixture was stirred at 50° C. for 45 minutes. A rapid dissolution was noted and the reaction mixture was brought to 20° C. and poured into water. The product was extracted with ethyl acetate and the extract was washed with saturated aqueous sodium chloride solution, dried and concentrated to dryness by distillation under reduced pressure. The 1.39 g of residue were chromatographed on silica and eluted with a mixture of cyclohexane and ethyl acetate (7:3) to obtain 916 mg of expected product.

| NMR Spectrum (CDCl$_3$) in ppm: | |
|---|---|
| H of Si Me$_2$ | 0.05 (s) |
| H of 18-Me | 0.79 (s) |
| H of tBu | 0.84 (s) |
| H of SMe | 2.51 (s) |
| H4 | 5.86 |
| Aromatic H atoms | 7.08 |

EXAMPLE 18

17$\beta$-[dimethyl-(1,1-dimethylethyl)-silyloxy]-7$\alpha$-[4-(methylthio)-phenyl]-$\Delta^{1,3,5(10)}$-estratrien-3-ol 0.49 ml of diisopropylamine and 10 ml of tetrahydrofuran were mixed under an inert atmosphere and 2.2 ml of a 1.65N suspension of n-butyllithium in hexane were added at 0° C. over approximately 5 minutes. The mixture was stirred for 30 minutes and 890 mg of 17$\beta$-[dimethyl-(1,1-dimethylethyl)-silyloxy]-7$\alpha$-[4-(methylthio)-phenyl]-$\Delta^4$-estren-3-one of Example 17 dissolved in 6 ml of tetrahydrofuran were introduced at −70° C. over approximately 20 minutes. The mixture was stirred for 30 minutes and 1.05 ml of trimethylsilyl chloride were introduced. The temperature was allowed to return to 20° C. and 600 mg of 2,3-dichloro-5,6-dicyanobenzoquinone and 1 ml of water were added. The reaction mixture stood at 20° C. for 16 hours and was poured into 50 ml of 2N aqueous sodium hydroxide solution. The product was extracted with ethyl acetate and the extract was washed with saturated aqueous sodium chloride solution dried and concentrated to dryness by distillation under reduced pressure. The 1.3 g of residue were chromatographed on silica and eluted with a mixture of toluene and ethyl acetate (95.5) to obtain 187 mg of expected product.

| IR Spectrum (chloroform) in cm$^{-1}$: |
|---|
| OH 3,610 |

EXAMPLE 19

7$\alpha$-[4-(methylthio)-phenyl]-$\Delta^{1,3,5(10)}$-estratrien-3-17$\beta$-diol 815 mg of 17$\beta$-[dimethyl-(1,1-dimethylethyl)-silyloxy]-7$\alpha$-[4,-(methylthio)-phenyl]-$\Delta^{1,3,5(10)}$-estratrien-3-ol of Example 18 were dissolved under an inert atmosphere in 6 ml of ethanol and 0.9 ml of 40% strength hydrofluoric acid were added. The mixture was stirred for 3 hours at 20° C. and the appearance of a precipitate was noted. The reaction mixture stood for 16 hours and was poured into aqueous sodium bicarbonate solution. The mixture was stirred and the precipitate formed was isolated by vacuum filtration, washed and dried to obtain 260 mg of crude product. 10 ml of boiling ethyl acetate were added thereto and the residual insoluble material was removed by filtration. The filtrate was concentrated to a small volume, added, cooled to 0° C. and stirred for 1 hour at 0° C. The precipitate formed was isolated by vacuum filtration washed and dried to obtain 94 mg of expected product melting at 186° C.

| NMR Spectrum (CDCl$_3$) in ppm: | |
|---|---|
| H of 18-Me | 0.80 (s) |
| H of SMe | 2.42 (s) |
| 17α H | 3.56 |
| H of OH | 4.85 |
| Aromatic H atoms | 6.63 to 7.16 |

EXAMPLE 20

7α-[4-(dimethylamino)-pheny]-19-nor-17α-Δ$^4$-pregnen-17β-ol-20-yn-3-one

STEP A:

7α-[4-(dimethylamino)-phenyl]-Δ$^{5(10)}$-estren-17β-ol-3-one-1,2-ethanediyl cyclic acetal and
7α-[4-(dimethylamino)-phenyl]-Δ$^5$-estren-17β-ol-3-one 3,3-(1,2-ethanediyl)-cyclic acetal 4 g of the product of Example 8 in 16 ml of ethylene glycol and 8 ml of ethyl orthoformate were heated at 75°/80° C. under an inert atmosphere for 2 and a quarter hours in the presence of 4 g of p-toluene-sulfonic acid dihydrate. The temperature was allowed to return to room temperature and the mixture was alkalinized using sodium bicarbonate and extracted with ethyl acetate. The extracts was washed with saline solution and dried and the solvents are removed under reduced pressure to obtain 7.49 g of crude product which was chromatographed on silica [eluent: petroleum ether (b.p. 40°–70° C.)/ethyl acetate 1:1] to obtain 3.07 g of expected Δ$^{5(10)}$ product and 0.470 g of expected Δ$^5$ product melting at 220° C.

STEP B:

7α-[4-(dimethylamino)-phenyl]-Δ$^{5(10)}$-estrene-3,17-dione 3,3-(1,2-ethanediyl)-cyclic acetal and
7α-[4-(dimethylamino-phenyl]-Δ$^5$-estrene-3,17-dione 3,3-(1,2-ethanediyl) cyclic acetal 2.63 g of the mixture of Step A in 50 ml of toluene were heated under reflux in an inert atmosphere with 1.2 g of aluminium isopropylate and 4 ml of cyclohexanone in 20 ml of toluene were then introduced over 3 hours while distillation was continued. The mixture was allowed to return to room temperature, was washed with saline solution and extracted with ethyl acetate. The extract was dried and the solvents were removed under reduced pressure to obtain 4.76 g of crude product which was chromatographed on silica [eluent: petroleum ether (b.p. 40°–70° C.)/ethyl acetate/triethylamine 60:40:0.1] to obtain 2.05 g of expected Δ$^{5(10)}$ product melting at 208° C. and 0.14 g of expected Δ$^5$ product melting at 210° C.

Δ$^{5(10)}$ product: analysis C$_{28}$H$_{37}$NO$_3$; molecular weight 425.61

Calculated: C% 77.20 H% 8.56 N% 3.22. Found: C% 77.3 H% 8.7 N% 2.9.

STEP C:

7α-[4-(dimethylamino)-phenyl]-19-nor-17α-Δ$^{5(10)}$-pregnen-17β-ol-20-yn-3-one, 1,2-ethanediylcyclic acetal Acetylene was bubbled for 1 hour into 17 ml of potassium tert-butylate dissolved to a concentration of 0.955N in tetrahydrofuran and 3.4 ml of hexamethylphosphoric triamide and 17 ml of tetrahydrofuran cooled to +4° C. 1.15 g of the Δ$^{5(10)}$ product of Step B dissolved in 20 ml of tetrahydrofuran were added and the mixture was allowed to return to room temperature, stirred for 2 hours and poured into ammonium chloride solution. The product was extracted with ethyl acetate and the extract was washed with saline solution and dried and the solvents were removed under reduced pressure at 50° C. to obtain 3.1 g of crude product which was chromatographed on silica (eluent: tolune/ethyl acetate/triethylamine 80:20:0.1) to obtain 1.35 g of expected product.

| IR Spectrum (CHCl$_3$) | |
|---|---|
| OH | 3601 cm$^{-1}$ |
| —C≡CH | 3306 cm$^{-1}$ |
| Aromatic | 1614–1556–1520 cm$^{-1}$ |

STEP D:

7α-[4-(dimethylamino)-phenyl]-19-nor-17αΔ$^4$-pregnen-17β-ol-20-yn-3-one 1.3 g of the product of Step C in 13 ml of methanol and 2.6 ml of 2N hydrochloric acid were heated to 35°–40° C. for 3 hours under an inert atmosphere. The methanol was removed under reduced pressure and the mixture was alkalinized using sodium bicarbonate and extracted with ethyl acetate. The extract was washed with saline solution, dried and taken to dryness under reduced pressure to obtain 1.17 g of crude product which was chromatographed on silica [eluant: petroleum ether (b.p. 40°–70° C.)/ethyl acetate 1:1] to obtain 0.81 g of expected product melting at 210° C.

Analysis: C$_{28}$H$_{35}$NO$_2$: molecular weight=417.60. Calculated: %C 80.53 %H 8.45 %N 3.35. Found: %C 80.6 %H 8.5 %N 3.2.

| IR Spectrum (CHCl$_3$) | |
|---|---|
| OH | 3601 cm$^{-1}$ |
| —C≡H | 3306 cm$^{-1}$ |
| Conjugated ketone | 1660 cm$^{-1}$ |
| Aromatic | 1614–1556–1520 cm$^{-1}$ |

EXAMPLE 21

7α-[4-(dimethylamino)-phenyl]-17α-(1-propynyl)Δ$^4$-estren-17β-ol-3-one

STEP A:

7α-[4-(dimethylamino)-phenyl]-17α-(1-propynyl)-Δ$^{5(10)}$estren-17β-ol-3-one 1,2-ethanediyl cyclic acetal Using the procedure of Step C of Example 20, 0.875 g of the product of Step B of Example 20 and replacing acetylene with methylacetylene were reacted and after the chromatography of 1.5 g of crude product, the expected product was collected.

| IR Spectrum (CHCl₃) | |
|---|---|
| OH | 3603 cm⁻¹ |
| —C≡C | 2240 cm⁻¹ |
| Aromatic | 1613–1560–1519 cm⁻¹ |

STEP B:
7α-[4-(dimethylamino)-phenyl]-17α-(1-propynyl)-Δ⁴estren-17β-ol-3-one Using the procedure of Step D of Example 20, 1.05 g of product of Step A were reacted to obtain 0.94 g of crude product which was chromatographed on silica [eluant: petroleum ether (b.p. 40°–70° C.)/ethyl acetate 4:6]. The residue was then dissolved in boiling methylene chloride and 9 ml of isopropyl ether was added. The mixture was partially concentrated, chilled and vacuum filtered. The product was dried at 50° C. under reduced pressure to obtain 0.49 g of expected product melting at 217° C.

Analysis: $C_{29}H_{37}NO_2$: molecular weight=431.63. Calculated: %C 80.70 %H 8.64 %N 3.24. Found: %C 80.6 %H 8.9 %N3.1.

| IR Spectrum (CHCl₃) | |
|---|---|
| OH | 3602 cm⁻¹ |
| —C≡H | 2235 cm⁻¹ |
| Conjugated ketone | 1660–883 cm⁻¹ |
| Aromatic | 1613–1522 cm⁻¹ |

EXAMPLE 22
7α-[4-(dimethylamino)-phenyl]-Δ⁴-estren-17β-ol-3-one
and
7β-[4-(dimethylamino)-phenol]-Δ⁴-estrene-17β-ol-3-one

STEP A:
17β-[dimethyl-(1,1-dimethylethyl)-silyloxy]-Δ⁴,⁶-estradien-3-one 74.55 g of Δ⁴,⁶-estradien-17β-ol-3-one, 4,6 g of imidazole and 49 g of tert-butyldimethylsilyl chloride in 210 ml of dimethylformamide were mixed at room temperature under an inert atmosphere. The mixture was heated to 50° C. for 2 and a quarter hours and then brought back to room temperature, poured into water and vacuum filtered. The product was dried under reduced pressure at 50° C. to obtain 110 g of crude product which was purified by chromatography on silica (eluant: cyclohexane/ethyl acetate 7:3) to obtain 92 g of the expected product melting at 110° C.

STEP B:
7α-[4-(dimethylamino)-phenyl]-17β-[dimethyl-(1,1-dimethylethyl)-silyloxy]-Δ⁴-estren-3-one 500 ml of 4-(dimethylamino)-phenylmagnesium bromide dissolved to a concentration of 0.9N in tetrahydrofuran were cooled to 0°/+5° C. under an inert atmosphere and 9 g of CuBrMe₂S were added. The mixture was stirred for 15 minutes and cooled to −65° C., and 20 ml of trimethylsilyl chloride were added followed over 40 minutes by 38.7 g of the product of Step A dissolved in 390 ml of tetrahydrofuran and 43 ml of hexamethylphosphoric triamide. The mixture was stirred for 45 minutes and 350 ml of 2N hydrochloric acid were added. The mixture was allowed to return to room temperature and was stirred for 105 minutes and alkalinized with 70 ml of concentrated ammonia solution. Settling was allowed to occur and the product was washed with saline solution and extracted with ethyl acetate. The extract was dried and the solvents were removed under reduced pressure to obtain 114 g of crude product which was purified by chromatography on silica [eluant: petroleum ether (b.p. 40°–70° C.)/ethyl acetate 8:2] to obtain 31 g of expected product.

STEP C:
7α-[4-dimethylamino)-phenyl]-Δ⁴-estren-17β-ol-3-one
and
7β-[4-(dimethylamino)-phenyl-Δ⁴-estren-17β-ol-3-one 90 ml of 2N hydrochloric acid were added to 31 g of the product of Step B suspended in 300 ml of methanol and the mixture was stirred for 1 hour at room temperature and poured into 300 ml of aqueous sodium bicarbonate solution. The product was extracted with ethyl acetate, washed with saline solution and dried, and the solvents were removed under reduced pressure. The residue was taken up in 20 ml of acetonitrile and crystallization was seeded. The mixture was chilled and vacuum filtered and the crystals were dried at 50° C. under reduced pressure to obtain 3.1 g of the expected product (7α isomer) identical with the product of Example 8 melting at 200° C.

26.3 g of product originating from the mother liquors were chromatographed on silica [eluant: petroleum ether (b.p. 40°–70° C.)/ethyl acetate 4:6] and the residue was crystallized from acetonitrile to obtain 4.45 g of 7α-isomer. Chromatography on silica of 1.34 g of residue originating from the mother liquors (eluant: acetonitrile/water 6:4) yielded 170 mg of the 7α-isomer and 160 mg of the 7β-isomer and 450 mg of a mixture of isomers.

Analysis of 7α-isomers: $C_{26}H_{35}O_2N$: molecular weight=379.57. Calculated: %C 79.35 %H 8.96 %N 3.56. Found: %C 79.2 %H 9.2 %N 3.5.

EXAMPLE 23
Example of pharmaceutical composition

Tablets corresponding to the following formula were prepared:
Product of Example 1: 100 μg
Excipient q.s. for a finished tablet weighing 100 mg (detail of the excipient: talc, starch, magnesium stearate).

PHARMACOLOGICAL STUDY

Antiproliferative activity of the products on the growth of MCF-7 mammary tumor cells.

Description of the Test (a) Cell Culture

MCF-7 lines were maintained in culture in FCS(1) medium at 37° C. in a humid atmosphere containing 5% CO₂ and the cells at subconfluence were harvested by trypsinization (0.05% trypsin, 0.02% EDTA), and then rinsed by gentle centrifugation. A sample of the cells in suspension was counted in a Malassez cell.

(b) Study of the Growth

The cells resuspended in the FCS medium were inoculated in the proportion of 30,000 cells per well in multiwell plates (24 2.5 cm² wells). Twenty-four hours after the inoculation (D0), the test product was added to the medium in ethanolic solution (final concentration in ethanol: 0.1%) at a concentration of $10^{-5}$M with the control wells receiving the same concentration of ethanol. The media were renewed every 48 hours. At the end of the experiment (D6), the medium was drawn off and the cells were immediately fixed with 150 μl of methanol to assay the DNA. The antiproliferative activity of the products was assessed by their capacity to inhibit the increase in DNA.

(c) DNA Assay

The DNA was assayed by a fluorimetric method using DABA (3,5-diaminobenzoic acid) (2). 150 μl of DABA were added to each well and the plates were then incubated for 45 min. at 56° C. and 1.5 ml of 1N HCl were then added. The fluorescence was measured using a fluorimeter (excitation wavelength: 400 nm; emission wavelength: 500 nm). The quantity of DNA per well was measured with respect to a calibration series obtained by treating a calf thymus DNA standard under the same conditions.

Results

The concentration in nM which inhibited the growth of the MCF-7 cells by 50% ($IC_{50}$) was determined in the manner stated above for the products of Examples 3, 4 and 6. The following results were obtained:

Product of Example 3: $IC_{50}$=0.1 nM
Product of Example 4: $IC_{50}$=100 nM
Product of Example 6: $IC_{50}$=10 nM (1) The foetal calf serum (FCS) culture medium was prepared as follows: MEM medium (Minimal Essential Medium) to which the following were added: non-essentialamino acids (GIBCO), penistrepto (penicillin 100 μl/ml, streptomycin 0.1 mg/ml), fungizone 0.1%, insulin (5 ng/ml), foetal calf serum (4% final concentration). Puzas and Goodman, Analytical Biochemistry, Vol. 86 pp. 50, 1978.

Various modifications of the compounds and methods of the invention may be made without departing from the spirit or scope thereof and it should be understood that the invention is intended to be limited only as defined in the appended claims.

What we claim is:
1. A 19-nor-steroid compound of the formula

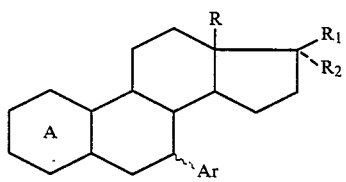

wherein the A ring is either

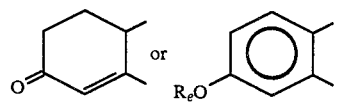

$R_e$ is selected from the group consisting of hydrogen, acyl and alkyl of 1 to 6 carbon atoms unsubstituted or substituted with amino or dialkylamino, R is methyl or ethyl, $R_1$ is selected from the group consisting of hydroxyl, protected hydroxyl, acyloxy and alkoxy of 1 to 4 carbon atoms, $R_2$ is selected from the group consisting of hydrogen, alkyl of 1 to 8 carbon atoms, alkenyl and alkynyl of 2 to 8 carbon atoms, acyl, aralkyl of 7 to 15 carbon atoms, the substituents other than hydrogen being unsubstituted or substituted with at least one member of the group consisting of halogen, alkyl of 1 to 4 carbon atoms for the aryl and aralkyl, methoxy, ethoxy, propyloxy, isopropyloxy and butyloxy, methylthio, ethylthio, propylthio, isopropylthio and butylthio, amino, methylamino, ethylamino, diemethylamino, diethylamino, methyl-ethylamino, each of the dialkyl-amino optionally being in oxidized form, aminomethyl or aminoethyl, dimethyl-aminomethyl, dimethylaminoethyl, dimethylaminoethyoxy, hydroxyl, acetoxy, a group of the formula

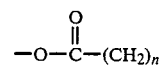

$CO_2H$ in which n=2 to 5, acetyl propionyl, butyryl, benzoyl, carboxy, methoxycarbonyl or ethoxycarbonyl, cyano, trifluoromethyl, aryl and aralkyl optionally substituted or $R_1$ and $R_2$ together form a group selected from the group consisting of

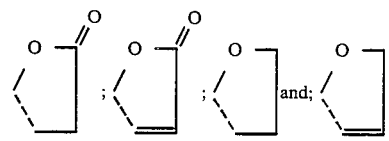

Ar is a 5- or 6-membered aryl selected from the group consisting of (a) phenyl unsubstituted or substituted with at least one member of the group consisting of halogen, alkyl, alkoxy, alkylthio of 1 to 4 carbon atoms, amino, alkylamino, dialkylamino, dialkylaminoalkoxyl, hydroxyl, acyl, free, esterified or salified carboxyl, cyano, trifluoromethyl, phenyl or benzyl unsubstituted or substituted with at least one alkyl of 1 to 4 carbon atoms and (b) a heterocyclic selected from the group consisting of thienyl, furyl, thiazolyl, isothiazolyl, oxazolyl, isoxazolyl, thiadiazolyl, pyridyl and piperidinyl or their salts with non-toxic, pharmaceutically acceptable bases or acids.

2. A compound of claim 1 wherein the A ring is

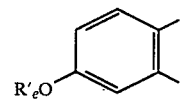

wherein $R'_e$ is hydrogen or alkyl of 1 to 4 carbon atoms.

3. A compound of claim 1 wherein $R_1$ is hydroxyl, unprotected or protected or acylated and $R_2$ is selected from the group consisting of alkyl, alkenyl and alkynyl, each unsubstituted or substituted with a member selected from the group consisting of halogens, hydroxyl, carboxyl optionally esterified or salified and cyano.

4. A compound of claim 1 selected from the group consisting of 7α-{4-[2-(dimethylamino)-ethoxy]-phenyl}-$\Delta^{1,3,5(10)}$-estratriene-3,17β-diol 7α-{4-[2-(dimethylamino)-ethoxy]-phenyl}-$\Delta^4$-estren-17β-ol-3-one 7β-{4-[2-(dimethylamino)-ethoxy]-phenyl}-$\Delta^{1,3,5(10)}$-estratriene-3,17β-diol 7β-{4-[2-(dimethylamino)-ethoxy]-phenyl}-$\Delta^4$-estren-17β-ol-3-one 7α-[4-(dimethylamino)-phenyl]-Δ$^{1,3,5(10)}$-estratriene-3,17β-diol 7α-(4-methoxyphenyl)-Δ$^{1,3,5(10)}$-estratriene-3,17β-diol 7α-[4-(methylthio)-phenyl]-Δ$^4$-estren-17β-ol-3-one and 7α-[4-(methylthio)-phenyl]-Δ$^{1,3,5(10)}$-estratriene-3,17β-diol.

5. An antiproliferative composition comprising an antiproliferatively effective amount of at least one compound of claim 1 and a pharmaceutical carrier.

6. A composition of claim 5 wherein A ring is

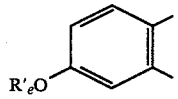

wherein Re is hydrogen or alkyl of 1 to 4 carbon atoms.

7. A composition of claim 5 wherein $R_1$ is hydroxy, unprotected or protected or acylated and $R_2$ is selected from the group consisting of alkyl, alkenyl and alkynyl, each unsubstituted or substituted with a member selected from the group consisting of halogens, hydroxyl, carboxyl optionally esterified or salified and cyano.

8. A composition of claim 5 wherein the active compound is selected from the group consisting of 7α-{4-[2-(dimethylamino)-ethoxy]-phenyl}-Δ$^{1,3,5(10)}$-estratriene-3,17β-diol 7α-{4-[2-(dimethylamino)-ethoxy]-phenyl}-Δ$^4$-estren-17β-ol-3-one 7β-{4-[2-(dimethylamino)-ethoxy]-phenyl}-Δ$^{1,3,5(10)}$-estratriene-3,17β-diol 7β-{4-[2-(dimethylamino)-ethoxy]-phenyl}-Δ$^4$-estren-17β-ol-3-one 7α-[4-(dimethylamino)-phenyl]-Δ$^{1,3,5(10)}$-estratriene-3,17β-diol 7α-(4-methoxyphenyl)-Δ$^{1,3,5(10)}$-estratrien-3,17β-diol 7α-[4-(methylthio)-phenyl]-Δ$^4$-estren-17β-ol-3-one and 7α-[4-(methylthio)-phenyl]-Δ$^{1,3,5(10)}$-estratriene-3,17β-diol.

9. A method of inhibiting cell proliferation in warm-blooded animals comprising administering to warm-blooded animals an antiproliferatively effective amount of at least one compound of claim 1.

10. A method of claim 9 wherein the A ring is

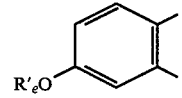

wherein Re is hydrogen or alkyl of 1 to 4 carbon atoms.

11. A method of claim 9 wherein $R_1$ is hydroxyl, unprotected or protected or acylated and $R_2$ is selected from the group consisting of alkenyl or alkynyl, each unsubstituted or substituted with a member selected from the group consisting of halogens, hydroxyl, carboxyl optionally esterified or salified and cyano.

12. A method of claim 9 wherein the active compound is selected from the group consisting of 7α-{4-[2-dimethylamino)ethoxy]-pheny}-Δ$^{1,3,5(10)}$-estratriene-3,17β-diol 7α-{4-[2-(dimethylamino)-ethoxy]-phenyl}-Δ$^4$-estren-17β-ol-3-one 7β-{4-[2-(dimethylamino)-ethoxy-phenyl}-Δ$^{1,3,5(10)}$-estratriene-3,17β-diol 7β-{4-[2-(dimethylamino)-ethoxy-phenyl}-Δ$^4$-estren-17β-ol-3-one 7α-[4-(dimethylamino)-phenyl]-Δ$^{1,3,5(10)}$-estratriene-3,17β-diol 7α-(4-methoxyphenyl)-Δ$^{1,3,5(10)}$-estratriene-3,17β-diol 7α-[4-(methylthio)-phenyl]-Δ$^4$-estren-17β-ol-3-one and 7α-[4-(methylthio)-phenyl]-Δ$^{1,3,5(10)}$-estratriene-3,17β-diol.

* * * * *